United States Patent [19]

Goy

[11] Patent Number: 5,413,581
[45] Date of Patent: May 9, 1995

[54] METHOD OF USING A BALLOON DILATATION CATHETER AND A GUIDEWIRE

[75] Inventor: Jean-Jacques Goy, Yverdon, Switzerland

[73] Assignee: Schneider (Europe) A.G., Bulach, Switzerland

[21] Appl. No.: 88,484

[22] Filed: Jul. 7, 1993

Related U.S. Application Data

[63] Continuation of Ser. No. 770,255, Oct. 2, 1991, abandoned.

[30] Foreign Application Priority Data

Oct. 4, 1990 [CH] Switzerland ............... 3204/90

[51] Int. Cl.$^6$ ............... A61M 29/02; A61M 31/00
[52] U.S. Cl. ............... 606/194; 604/53; 604/102
[58] Field of Search ............... 604/96–103, 604/283, 52, 53, 49–55; 606/192–196; 600/18

[56] References Cited

U.S. PATENT DOCUMENTS

| | | | |
|---|---|---|---|
| 4,195,637 | 4/1980 | Gruntzig et al. | |
| 4,332,254 | 6/1982 | Lundguist | 606/194 |
| 4,601,706 | 7/1986 | Aillón | 604/122 |
| 4,774,949 | 10/1988 | Fogarty | 606/194 X |
| 4,782,834 | 11/1988 | Maguire et al. | |
| 4,892,519 | 1/1990 | Songer et al. | 604/96 |
| 4,896,670 | 1/1990 | Crittendon | 606/194 |
| 4,909,258 | 3/1990 | Kuntz et al. | 128/658 |
| 4,944,745 | 7/1990 | Sogard et al. | |
| 5,042,985 | 8/1991 | Elliott et al. | 606/192 |
| 5,045,061 | 9/1991 | Seifert et al. | 604/96 |
| 5,059,177 | 10/1991 | Towne et al. | 604/96 |
| 5,090,958 | 2/1992 | Sahota | 604/98 |

FOREIGN PATENT DOCUMENTS

| | | |
|---|---|---|
| 0244955 | 11/1987 | European Pat. Off. . |
| 0277370 | 8/1988 | European Pat. Off. . |
| 90734 | 11/1937 | Switzerland ............... 604/95 |

Primary Examiner—Adam J. Cermak
Attorney, Agent, or Firm—Peter C. Richardson; Lawernce C. Akers; Philip C. Strassberger

[57] ABSTRACT

The balloon dilatation catheter has a first lumen extending along the entire length of a shaft, which lumen is connected to a pump and, at the distal end of the catheter, to the inside of the balloon. Through this lumen there also passes a support wire connected firmly to the catheter. The shaft has an additional lumen which opens outwards via an opening behind the proximal end of the balloon. A controllable guide wire can be introduced into this lumen via an attachment piece. Similarly, a measuring apparatus or an apparatus for introducing a contrast medium or drug can be connected to this additional lumen. The catheter is particularly suitable for treating strictures in an arterial ramification.

1 Claim, 2 Drawing Sheets

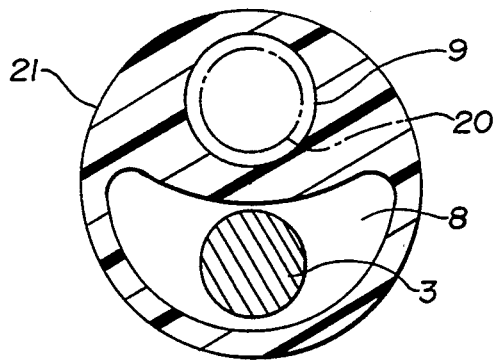
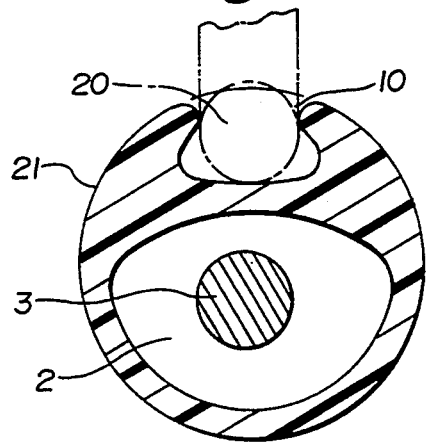
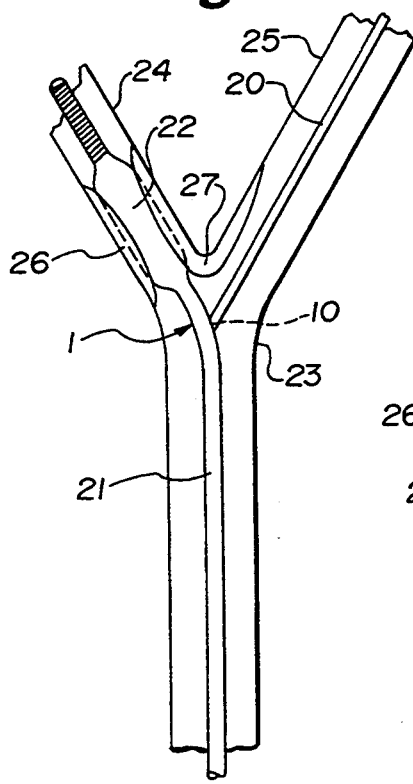
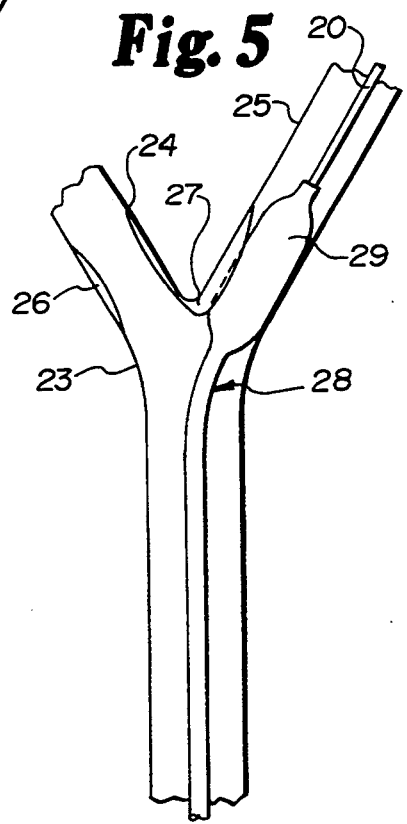
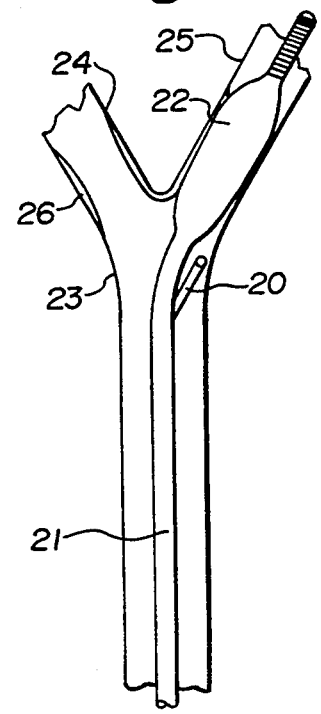

METHOD OF USING A BALLOON DILATATION CATHETER AND A GUIDEWIRE

This is a continuation of application Ser. No. 07/770,255, filed on Oct. 2, 1991, now abandoned.

BACKGROUND OF THE INVENTION

The invention relates to a balloon dilatation catheter for percutaneous transluminal angioplasty.

Catheters of this type have been known for a long time under the designation "PTCA catheters" for the treatment of strictures in blood vessels and have generally proven themselves in this respect. However, the treatment of strictures or stenoses in ramifications is very difficult and complex using the known catheters. The two methods below have in particular become well known.

In the so-called "kissing balloon" technique, two balloon dilatation catheters are introduced percutaneously at the same time. The distal ends of the dilatation catheters separate in front of the ramification in such a way that a balloon comes to lie in each branch of the ramification. The proximal ends of the two balloons touch while doing this. Both balloon dilatation catheters are generally dilated at the same time for dilatation of the stenosis. This method and the catheter designed for it are described in EP-A 0,347,023.

In the other treatment method, two identical guide wires are introduced, again percutaneously, and in such a way that they separate in front of the ramification. On the one guide wire, a so-called "monorail" catheter is now first introduced into one branch of the ramification. The stricture site in this branch is dilated using the balloon of the catheter, and the catheter is thereafter completely withdrawn. On the other guide wire, a further balloon dilatation catheter of this type is now introduced into the other branch of the ramification, and the stricture in this other branch is now dilated. One advantage of this method is that the time necessary for fluoroscopy can be reduced. The treatment time can therefore be kept especially short using this method.

SUMMARY OF THE INVENTION

The aim of the invention is to provide a balloon dilatation catheter of the stated generic type, which catheter permits an even simpler, yet reliable treatment of strictures in arterial ramifications and which nevertheless can be produced simply and inexpensively. The aim is achieved by the claimed invention. The balloon dilatation catheter according to the invention thus has in the shaft an additional lumen opening outwards before the proximal end of the balloon. This lumen is connected at the proximal end of the shaft to an attachment piece through which a guide wire can be introduced into this additional lumen. For treating a stenosis at an arterial ramification, the balloon dilatation catheter according to the invention is introduced into one of the branches of the ramification and the guide wire is introduced into the other branch via the additional lumen. The stricture in this branch is dilated as usual by expanding the balloon. If no further dilatation is necessary, then the catheter is completely withdrawn as usual. However, if dilatation is also necessary in the other branch of the ramification, then the catheter is withdrawn and further, conventional dilatation catheter is introduced into the further branch to be dilated, via the guide wire already inserted. The important point is that the guide wire should ensure that, even after dilatation of the first branch, a catheter can be introduced into the second branch which may possibly be further constricted. Moreover, a drug or a contrast medium can be introduced through the said additional lumen with or without the guide wire inserted. Similarly, a blood pressure measurement or another measurement is possible via this additional lumen.

In further development of the invention, the balloon dilatation catheter according to the invention has a support wire connected firmly to the balloon or the shaft. Balloon dilatation catheters with a support wire are known per se and have the advantage that they can be produced with a very small profile, since no shaft is required in the balloon. However, a disadvantage of this catheter is that introduction of contrast media or drugs or measurement of blood pressure is not possible. However, in the design according to the invention, a treatment agent can be introduced into the vessel or a measurement carried out at any time via the additional lumen. The balloon dilatation catheter according to the invention can therefore also be advantageous for the treatment of strictures which are not located in vessel ramifications. In such cases the rigidity of the catheter can be increased, if so desired, by introducing a guide wire into the additional lumen. The simultaneous presence of the support wire and of the guide wire then gives the catheter a particularly high degree of rigidity.

In a further development of the invention, the shaft has at least one opening immediately before the proximal end of the balloon, through which opening the additional lumen opens outwards. In this embodiment the additional lumen thus extends essentially along the entire length of the shaft. A guide wire introduced into this lumen accordingly strengthens the shaft essentially along its entire length.

The invention also relates to a device with a balloon dilatation catheter for percutaneous transluminal angioplasty and an exchangeable guide wire. This device is characterized in that a first attachment piece is arranged at the proximal end of the shaft, this attachment piece having a junction for the attachment of a pump for dilating or folding the balloon and a junction for a second attachment piece. The second attachment piece has a junction for the attachment of a measuring apparatus or an apparatus for feeding a contrast medium or drug into the additional lumen of the shaft, and an inlet for introducing the guide wire likewise into the additional lumen. Such a device makes it possible to carry out, independently of one another, measurements or infusions via the additional lumen and control of the pressure in the balloon via the first lumen. The guide wire can be introduced via the additional lumen irrespective of the pressure in the balloon. These functions are also possible when the catheter has a fixed support wire.

Further advantageous features will emerge from the following description. An exemplary embodiment of the invention is illustrated in greater detail below with reference to the drawings, in which:

BRIEF DESCRIPTION OF THE DRAWINGS

FIG. 2 shows a section along line II—II in FIG. 1, FIG. 3 shows a section along line III—III in FIG. 1, FIG. 4 shows, diagrammatically, a stenosed arterial ramification with the catheter according to the invention introduced, and FIG. 5 and 6 show the arterial ramification according to FIG. 4, but during treatment of the other branch.

DETAILED DESCRIPTION OF A PREFERRED EMBODIMENT

Figure 1:
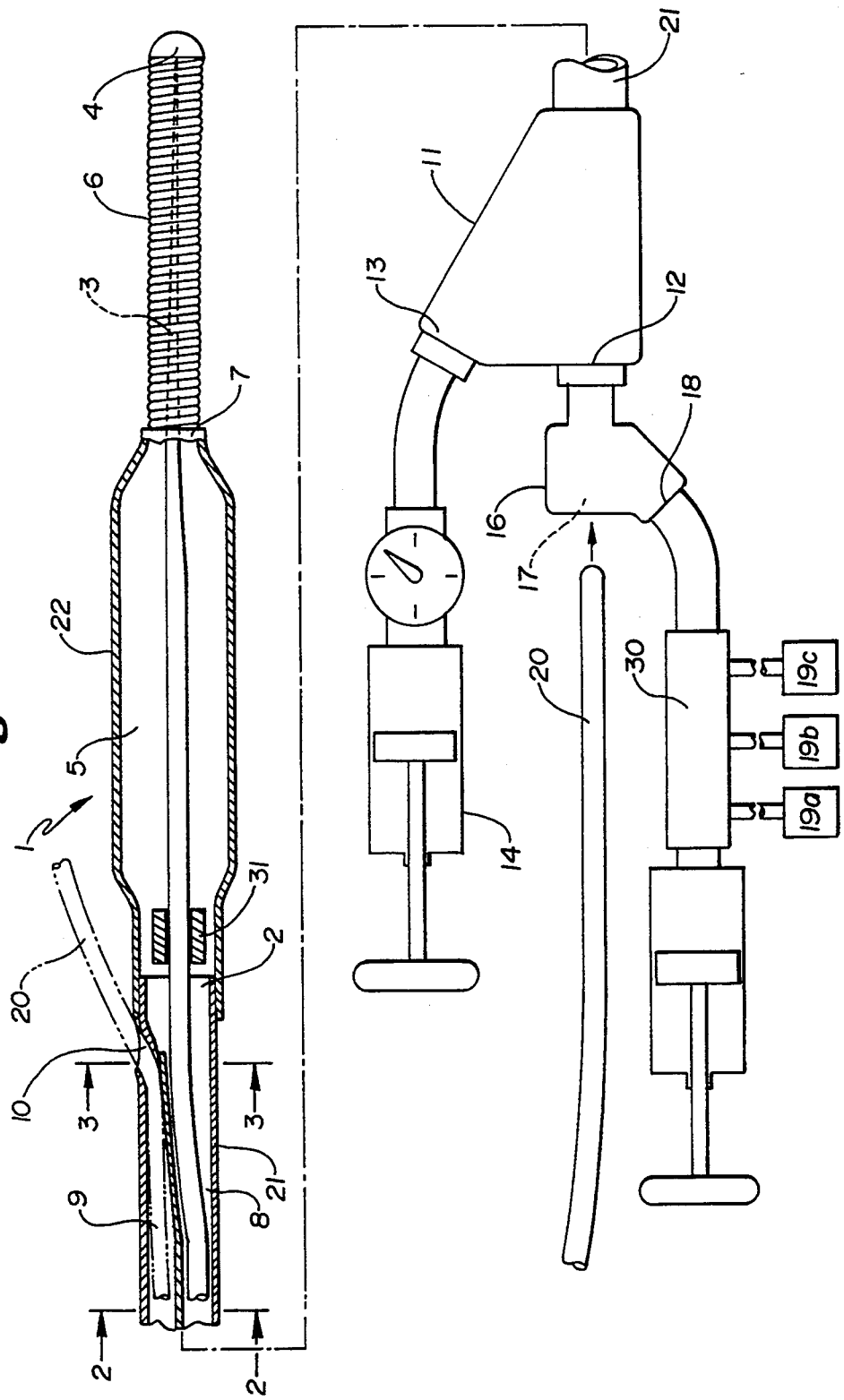
FIG. 1 shows partially in longitudinal section a catheter device according to the invention.

The catheter device shown in FIG. 1 consists of a balloon dilatation catheter 1, and exchangeable guide wire 20, a pump 14 and an apparatus 19 for blood pressure measurement or for introduction of contrast medium or drugs.

The balloon dilatation catheter 1 has at its distal end a balloon 22 which, at its proximal end, is pushed onto a shaft 21 and is thermoplastically welded or glued to the latter. The balloon 22 consists for example of a suitable polyamide, polyethylene terephthalate or another suitable polymer. It preferably has a narrow profile. For its dilatation, the inside 5 of the balloon 22 is filled with a fluid at a pressure of, for example, 8 bar. In addition, the inside 5 is connected to the pump 14 via an opening 2 and a first lumen 8.

At the distal end the balloon 22 is connected firmly to a flexible spiral spring 6 at position 7. Inside this spring 6 there extends the distal end of a support wire 3 which at its tip, at position 4, is soldered to the spiral spring 6. The support wire 3 is conically tapered in the region of the balloon 22 and of the spiral spring 6. The support wire 3 extends in the first lumen 8, preferably along the entire length of the shaft 21, and is firmly connected at its proximal end to the shaft 21. The support wire 3 provides for the transmission of torque from the proximal to the distal end of the catheter 1 during its introduction. Together with the spiral spring 3, it permits the introduction of the balloon 22 into vessel bends or into a branch of a ramification. Appropriate markings 31 at the distal end of the balloon dilatation catheter 1 allow the position of the balloon 22 to be monitored in a known manner.

The shaft 21 has a second lumen 9 which extends along the entire length of the shaft and which, in accordance with FIG. 2, preferably has a round cross-section. The lumen 9 opens outwards directly behind the proximal end of the balloon 22 via an opening 10. The lumen 9 and the inside 5 of the balloon are thus separated from each other. At its proximal end the second lumen 9 is connected to an attachment piece 16. This attachment piece 16 has a fluid-tight tap system 30, with which the lumen 9 can be connected via a junction 18 alternatively for blood pressure measurement, for injection of a contrast medium or of a drug, using one of the apparatuses 19. The guide wire 20 can be pushed into the lumen 9 through the opening 17 in which a sealing membrane is arranged.

The shaft 21 can similarly be produced from a suitable polyamide, polyethylene or another suitable thermoplastic polymer. Its external diameter is 1.2 mm for example and its length 130 cm for example. The internal diameter of the circular lumen 9 is preferably about 0.4 mm and the external diameter of the guide wire 20 is preferably about 0.35 mm. The narrowest width of the first lumen 8 is preferably about 0.5 mm. The external diameter of the support wire 3 is correspondingly slightly smaller in the region of the shaft 21. As FIGS. 2 and 3 show, the cross-section of the first lumen 8 is semicircular or crescent-shaped so that, even in the case of a small external diameter of the shaft 21, pressure fluid for the balloon 22 can circulate in the lumen 8. As is shown, the shaft 21 preferably has two lumina, but embodiments are conceivable in which the shaft 21 has more than two lumina.

At its proximal end, the shaft 21 is connected to a first attachment piece 11 to the second attachment piece 16. The first attachment piece 11 has in known manner two junctions 12 and 13, junction 12 providing for the connection of the lumen 9 to the attachment piece 16 and junction 13 providing for the connection of the lumen 8 to the pump 14. Such attachment pieces 11 are well known per se.

A preferred use of the balloon dilatation catheter and of the catheter device is illustrated in greater detail below with reference to FIGS. 4 and 5.

An arterial ramification 23 has a left branch 24 and a right branch 25. The ramification is narrowed by stenosed areas 26 and 27. In order to reopen the ramification point, both branches 24 and 25 are dilated. The two following methods are now possible using the catheter device according to the invention.

In a first method, the balloon 22 of the catheter 1 is introduced for example into the branch 24. Since, as mentioned above, the catheter 1 has a support wire 3, which is essentially a fixed guide wire 3, the catheter 1 can be guided and the balloon 22 can be introduced into the branch 24. The guide wire 20 is then introduced into the catheter and advanced in such a way that it protrudes through the stricture 27 into the branch 25, as shown in FIG. 4. The distal end of the guide wire 20 thus projects outwards through the opening 10 in the shaft 21 and into the branch 25. The guide wire 20 is a controllable guide wire known per se. When the balloon 22 is in the desired position, then the stenosing area 26 can be forced radially outwards in a known manner by dilating the balloon 22. During this, the branch 25 is usually further constricted. However, the applied wire 20 prevents a complete narrowing and ensures that the branch 25 remains open for the introduction of a further catheter. After dilating the branch 24, the catheter 1 is completely withdrawn, so that only the guide wire 20 is still in place. A conventional balloon dilatation catheter 28 is then introduced via the guide wire 20, and the balloon 29 is pushed into the branch 25 so that the stricture 27 can be dilated. The introduction of the catheter 28 is simple, since it is guided through the guide wire 20 already in place. After dilating the stricture 27, the catheter 28 is removed together with the guide wire 20. However, it is also possible to remove only the catheter 28 and to introduce a catheter 1 into the branch 24 again, in order to dilate this once more.

In the second method, a guide wire 20 is first introduced into one of the branches 24 or 25, and a balloon 29 of a conventional catheter 28 is introduced into the corresponding branch on this wire. Thus, in this method, one of the branches 24 or 25 is first dilated with the conventional balloon dilatation catheter 28, as is shown diagrammatically in FIG. 5. The catheter 28 is then completely withdrawn, the guide wire 20 remaining in the vessel. The catheter 1 according to the invention is then introduced on the guide wire 20 in such a way that its balloon 22 is situated in the other branch, as shown in FIG. 4. When the balloon 22 is positioned, this other branch is dilated by it, as described above. The catheter 1 and the guide wire 20 are then completely withdrawn.

According to a third method the one branch is dilated as shown in FIG. 4. For the treatment of the other branch 25, the catheter 1 is now so far withdrawn to enable the introduction of the balloon 22 into the other branch 25. The balloon 22 is then disposed near the distal end of the guide wire 20 in branch 25, as shown in FIG. 6. The balloon 22 is now inflated and the branch 25 dilated.

I claim:

1. A method for dilating a stenosis in each of a pair of branch coronary arteries comprising:

introducing into a first branch coronary artery a steerable balloon dilatation catheter having a shaft with a distal end and a proximal end and a first lumen extending through the shaft, a balloon with a distal end and a proximal end arranged at the distal end of the shaft, the first lumen being in communication with the balloon, a first guidewire extending through and fixed within the first lumen and a second lumen extending through a portion of the shaft and having an opening outwards of the shaft before the proximal end of the balloon, the second lumen being adapted to have a second guidewire pass therethrough;

advancing the second guidewire through the second lumen and through the opening into a second branch coronary artery;

inflating the balloon to effect a dilatation of a stenosis in the first branch coronary artery;

deflating the balloon;

withdrawing the steerable balloon dilatation catheter from the first branch coronary artery while maintaining the second guidewire in the second branch coronary artery;

advancing a balloon dilatation catheter over the second guidewire into the second branch coronary artery; and inflating the balloon of the balloon dilatation catheter to effect a dilatation of a second stenosis in the second branch coronary artery.

* * * * *